US012567140B2

(12) United States Patent (10) Patent No.: US 12,567,140 B2
Lee et al. (45) Date of Patent: Mar. 3, 2026

(54) METHOD AND APPARATUS FOR ANALYZING BODY COMPOSITION USING MEDICAL IMAGE

(71) Applicant: MEDICALIP CO., LTD., Gangwon-do (KR)

(72) Inventors: Hyuk Hee Lee, Seoul (KR); Soon Ho Yoon, Seoul (KR); Doo Hee Lee, Seoul (KR)

(73) Assignee: MEDICALIP CO., LTD., Chuncheon-si (KR)

( * ) Notice: Subject to any disclaimer, the term of this patent is extended or adjusted under 35 U.S.C. 154(b) by 225 days.

(21) Appl. No.: 17/310,311

(22) PCT Filed: May 6, 2021

(86) PCT No.: PCT/KR2021/005668
§ 371 (c)(1),
(2) Date: Jul. 27, 2021

(87) PCT Pub. No.: WO2022/158654
PCT Pub. Date: Jul. 28, 2022

(65) Prior Publication Data
US 2023/0368373 A1 Nov. 16, 2023

(30) Foreign Application Priority Data
Jan. 20, 2021 (KR) ........................ 10-2021-0008102

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/62* (2017.01); *G06V 10/774* (2022.01);
(Continued)

(58) Field of Classification Search
None
See application file for complete search history.

(56) References Cited

U.S. PATENT DOCUMENTS

2016/0361025 A1* 12/2016 Reicher ................... G16Z 99/00
2018/0192944 A1* 7/2018 Diener ................. A61B 5/4872
(Continued)

FOREIGN PATENT DOCUMENTS

CN 109598728 A 4/2019
CN 111462055 A * 7/2020 .............. G06N 3/04
(Continued)

OTHER PUBLICATIONS

Office Action, dated Apr. 12, 2021, issued for Korean Patent Application No. 10-2021-0008102, 12 pages (with English translation).

*Primary Examiner* — Delomia L Gilliard

(74) *Attorney, Agent, or Firm* — Klarquist Sparkman, LLP

(57) ABSTRACT

Provided are a method and an apparatus for analyzing a body composition by using a medical image. The apparatus for analyzing the body composition trains a first artificial intelligence model by using training data labelling a body tissue region, such as muscle or fat, in a medical image for training, and then, segments a body tissue from an examination medical image by using the first artificial intelligence model and outputs body composition information based on a region, a volume, or a weight of the body tissue of the examination medical image. The disclosure is a technique developed through the Seoul Business Agency's 2020 support project for artificial intelligence (AI) technology industrialization (CY20053), "AI Verification and Industrialization of Computed Tomography (CT) Image-based (Continued)

Opportunistic Screening of Metabolic Syndrome, Osteoporosis, and Muscle Reduction."

13 Claims, 11 Drawing Sheets

(51) Int. Cl.
| | |
|---|---|
| *G06T 7/62* | (2017.01) |
| *G06V 10/774* | (2022.01) |
| *G16H 30/40* | (2018.01) |
| *G16H 50/20* | (2018.01) |

(52) U.S. Cl.
CPC ............. G16H 30/40 (2018.01); G16H 50/20 (2018.01); *G06T 2207/10081* (2013.01); *G06T 2207/30012* (2013.01); *G06T 2207/30088* (2013.01); *G06T 2207/30101* (2013.01); *G06V 2201/033* (2022.01)

(56) References Cited

U.S. PATENT DOCUMENTS

| | | | |
|---|---|---|---|
| 2021/0059627 A1 | | 3/2021 | Kim et al. |
| 2021/0241027 A1* | | 8/2021 | Hu ............................ G06T 7/11 |

FOREIGN PATENT DOCUMENTS

| | | | | |
|---|---|---|---|---|
| JP | 2020119510 | A | | 8/2020 |
| KR | 20200021733 | A | * | 8/2018 |
| KR | 101981202 | B1 | * | 12/2018 |
| KR | 2020108686 | A | * | 3/2019 |
| KR | 10-2020-0021733 | A | | 3/2020 |
| KR | 10-2084598 | B1 | | 3/2020 |
| KR | 10-2020-0108686 | A | | 9/2020 |

* cited by examiner

600

610

700

710

METHOD AND APPARATUS FOR ANALYZING BODY COMPOSITION USING MEDICAL IMAGE

CROSS REFERENCE TO RELATED APPLICATIONS

This is the U.S. National Stage of International Application No. PCT/KR2021/005668, filed May 6, 2021, which claims priority to Korean Patent Application No. 10-2021-0008102, filed Jan. 20, 2021, which applications are incorporated by reference herein in their entireties.

TECHNICAL FIELD

One or more embodiments relate to analyzing a body composition, and more particularly, to a method and an apparatus for analyzing a body composition by using a medical image.

BACKGROUND ART

Generally, a body composition analysis is performed by calculating the amount of body fat, muscle mass, etc., by measuring the body bioimpedance. Bioimpedance measurement is a method of estimating the amount of muscle mass and fat by connecting an electrode to a body of a subject that is measured and measuring a resistance by applying a minute current to the electrode. However, with respect to the bioimpedance measurement, the accuracy of measurement varies according to a motion or a degree of muscular tension of the measured subject during the measurement. Also, problems regarding measuring a skin area or a composition of an internal organ, a bone, etc. arise.

Disclosed is a technique developed through the Seoul Business Agency's 2020 support project for artificial intelligence (AI) technology industrialization (CY20053), "AI Verification and Industrialization of Computed Tomography (CT) Image-based Opportunistic Screening of Metabolic Syndrome, Osteoporosis, and Muscle Reduction."

DESCRIPTION OF EMBODIMENTS

Technical Problem

A technical objective to be achieved by the disclosure is to provide a method and an apparatus for accurately measuring a body composition by using a medical image.

Solution to Problem

According to one or more embodiments, a method of analyzing a body composition by using a medical image includes: training a first artificial intelligence model by using training data labelling at least one body tissue region from among a skin, a bone, an internal organ, a blood vessel, muscle, and fat in a training medical image; receiving an examination medical image; segmenting a body tissue from the examination medical image by using the first artificial intelligence model; and outputting body composition information recognized based on a region, a volume, or a weight of the body tissue of the examination medical image.

According to one or more embodiments, an apparatus for analyzing a body composition includes: a first artificial intelligence model trained by using training data labelling at least one body tissue region from among a skin, a bone, an internal organ, a blood vessel, muscle, and fat in a medical image; a first classifier configured to segment a body tissue, such as the muscle, the fat, or the bone, by inputting an examination medical image to the first artificial intelligence model; and a body composition recognizer configured to recognize and output body composition information based on the segmented body tissue.

Advantageous Effects of Disclosure

According to an embodiment of the disclosure, a body composition of the entirety or part of a human body may be accurately identified by analyzing a medical image. Because the body composition is identified from the medical image, a past body composition of a subject may also be identified when there is an available past medical image of the subject. Also, by using medical images accumulated during a predetermined period of time, a change in the body composition during the predetermined period of time may be identified.

MODE OF DISCLOSURE

Hereinafter, a method and an apparatus for analyzing a body composition by using a medical image, according to an embodiment, will be described in detail by referring to the accompanying drawings.

Figure 1:
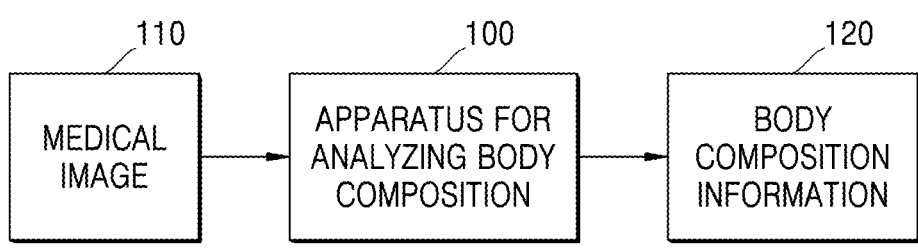
FIG. 1 is a diagram of an example of an apparatus for analyzing a body composition, according to an embodiment.

FIG. 1 is a diagram of an example of an apparatus 100 for analyzing a body composition according to an embodiment.

Referring to FIG. 1, the apparatus 100 for analyzing the body composition may receive a medical image 110 and analyze and output a body composition from the medical image 110. The apparatus 100 for analyzing the body composition may be realized as various types of computing devices including a processor, a memory, input and output devices, etc., a cloud system, or the like. As another example, the apparatus 100 for analyzing the body composition may be realized as part of medical equipment, such as a computed tomography (CT) apparatus. In addition thereto, the apparatus 100 for analyzing the body composition may be realized in various forms, for example, as various storages (for example, a universal serial bus (USB) memory, etc.) including software in which a method according to the present embodiment is realized.

The medical image 110 is a three-dimensional medical image in which a cross-section of a human body is captured. Examples of the three-dimensional medical image may include a CT image, a magnetic resonance imaging (MRI) image, etc. Furthermore, the medical image 110 may be images in various forms, in which a cross-section of a human body is captured. Hereinafter, a medical image used for training an artificial intelligence (AI) model will be referred to as a training medical image, and a medical image used for recognizing a body composition will be referred to as an examination medical image.

Figure 9:
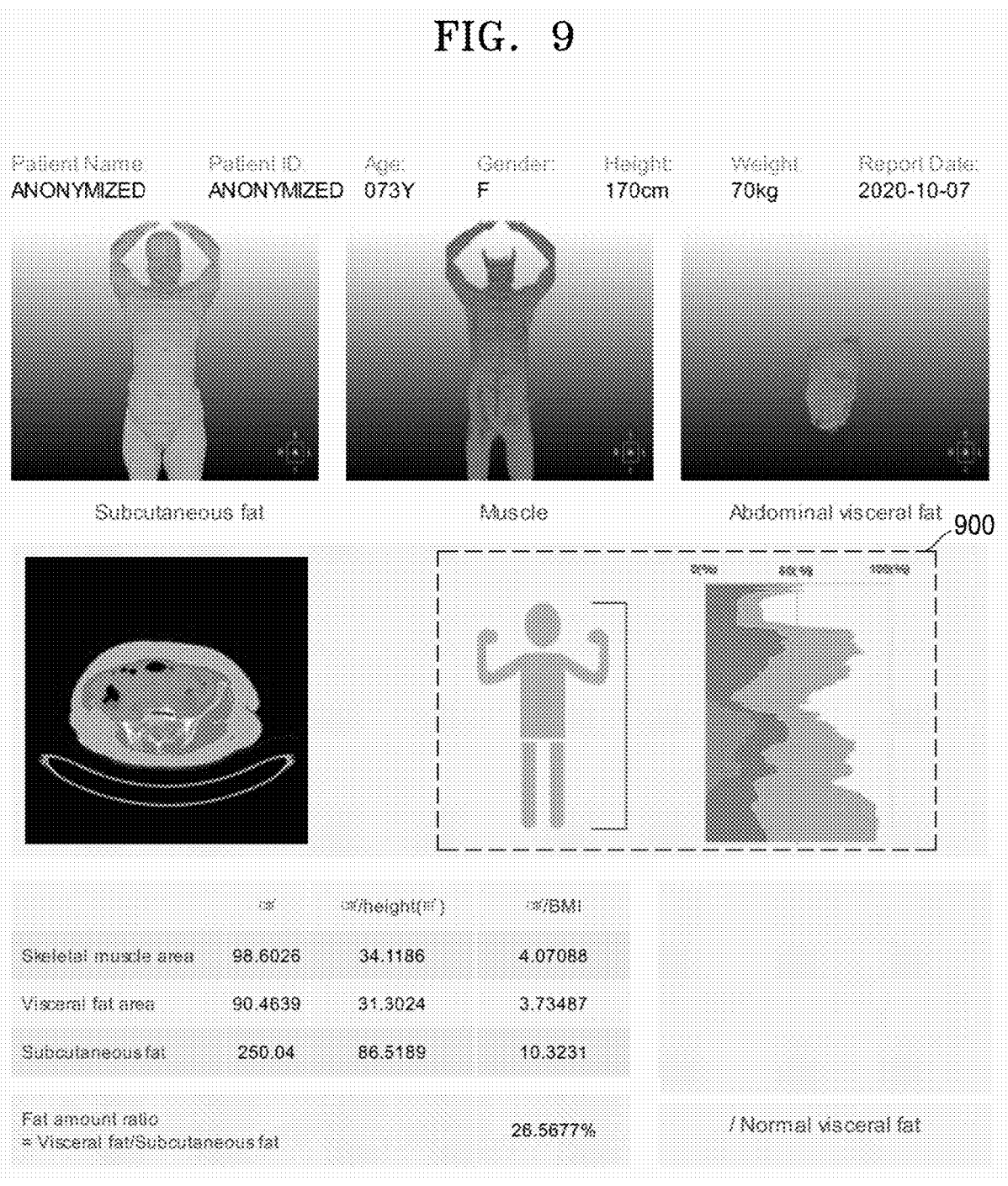
FIG. 9 is a diagram of an example of biometric information according to an embodiment.

Body composition information 120 refers to various information about a body tissue, such as a region, a weight, or a volume of the body tissue, the amount of fat, muscle mass, skeletal muscle mass, or visceral fat of a human body, a volume or a skin region of a specific organ, or the like. The apparatus 100 for analyzing the body composition may output the body composition information 120 in various forms, such as text, a graph, etc., and an example thereof is illustrated in FIG. 9.

Figure 2:
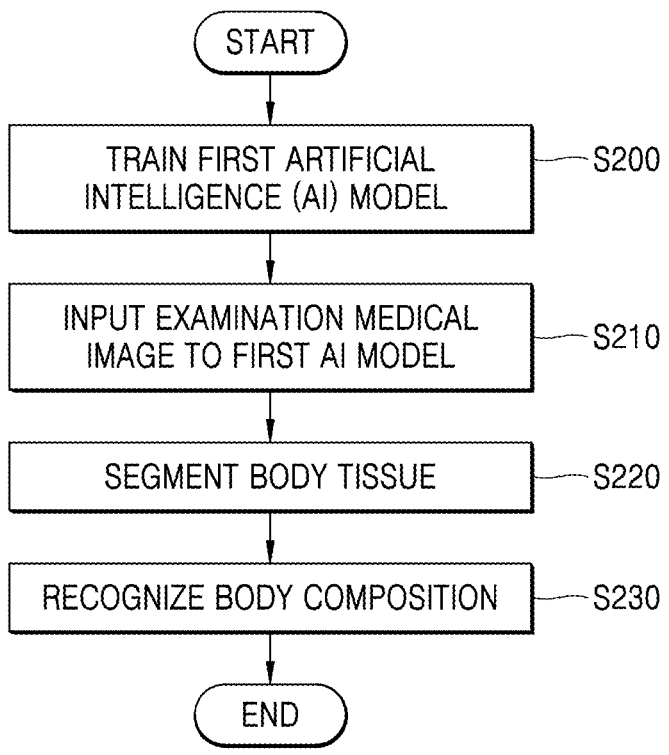
FIG. 2 is a flowchart of an example of a method of analyzing a body composition, according to an embodiment.

FIG. 2 is a flowchart of an example of a method of analyzing a body composition, according to an embodiment.

Referring to FIG. 2, the apparatus 100 for analyzing the body composition may train a first AI model configured to segment at least one body tissue from among a skin, a bone, an internal organ, a blood vessel, muscle, and fat in a medical image (S200). An example of the first AI model is illustrated in FIGS. 3 and 4.

The apparatus 100 for analyzing the body composition may input an examination medical image into the first AI model on which training is completed, and segment a body tissue, such as fat, muscle, etc. (S210). For example, the examination medical image may include a plurality of CT images with respect to the entirety or part of a human body, and the apparatus 100 for analyzing the body composition may input the plurality of CT images into the first AI model and may obtain a segmentation result of a body tissue, such as a skin, an internal organ, fat, or muscle, in each CT image.

The apparatus 100 for analyzing the body composition may recognize a region, a volume, a weight, or the like of the body tissue segmented in the medical image by using the first AI model or may recognize body composition information by using the recognized information (S230). For example, when the examination medical image includes a plurality of CT images with respect to a cross-section of a human body, the apparatus 100 for analyzing the body composition may obtain a volume by using a region of a body tissue, such as an internal organ, fat, muscle, etc., obtained from each CT image and a gap between each CT image, may obtain a weight of each body tissue by using the volume and a density of the body tissue (that is, a density of a specific internal organ, fat, muscle, or the like), or may identify texture of the body tissue by using a brightness value.

Figure 3:
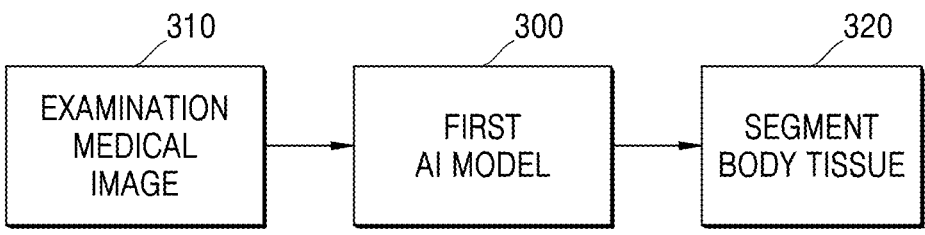
FIGS. 3 and 4 are diagrams of an example of a first artificial intelligence (AI) model according to an embodiment.
Figure 4:
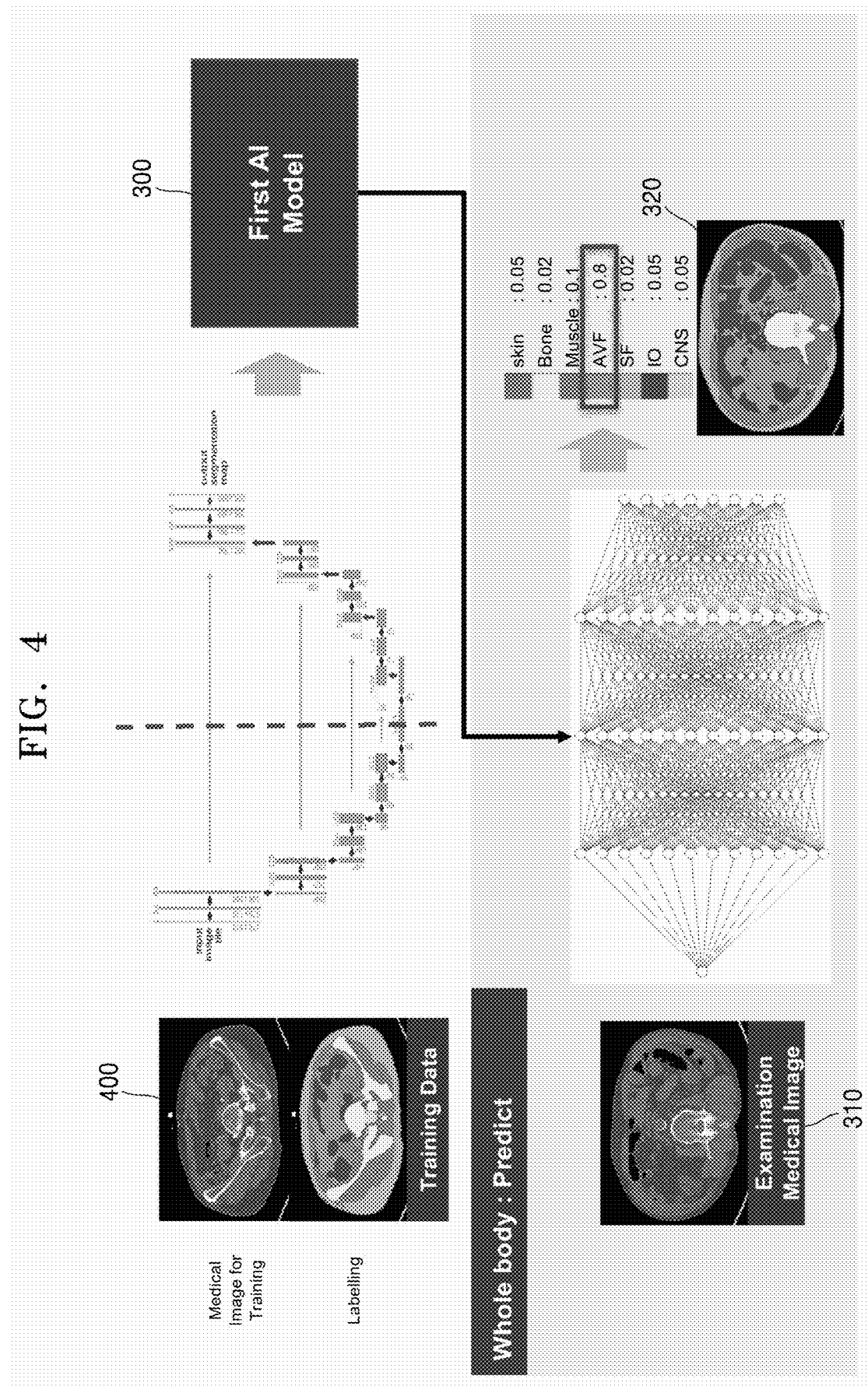

FIGS. 3 and 4 are diagrams of an example of a first AI model according to an embodiment.

Referring to FIGS. 3 and 4 together, a first AI model 300 may be a model generated via a learning process, such as deep learning, machine learning, etc. The first AI model 300 may be realized as various architectures, such as a convolution neural network (CNN), a DenseNet, a U-net, a GoogLeNet, a generative adversarial network, etc. For example, when the first AI model 300 is realized as a CNN, the first AI model 300 may perform a learning process of adjusting a connection weight value of an artificial network by using training data 400.

The first AI model 300 may be trained by using the training data 400 labelling at least one body tissue area from among a skin, a bone, an internal organ, a blood vessel, muscle, and fat. For example, to generate the first AI model 300 configured to segment a fat region from a medical image, the first AI model 300 may be trained by using the training data 400 labelling the fat region in a training medical image. As another example, to generate the first AI model 300 configured to simultaneously segment a plurality of body tissues, such as a skin, fat, muscle, bones, or neurons, the first AI model 300 may be trained by using the training data 400 labelling, in the training medical image, each of the body tissues to be segmented.

When the first AI model 300 completely trained receives an examination medical image 310, the first AI model 300 may output a result 320 of segmenting each body tissue from the examination medical image 310. According to another embodiment, the result 320 of segmenting the body tissue from the examination medical image 310 may be used as training data for additional training of the first AI model 300.

Figure 5:
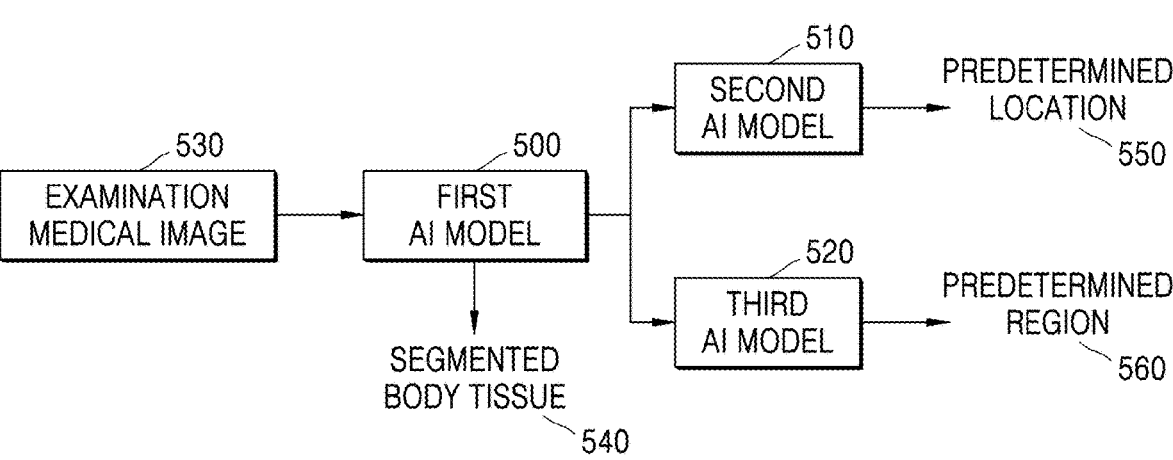
FIG. 5 is a diagram of an example of a method of identifying a body composition with respect to a part of a human body, according to an embodiment.

FIG. 5 is a diagram of an example of a method of recognizing a body composition with respect to a specific part of a human body, according to an embodiment.

Referring to FIG. 5, the apparatus 100 for analyzing the body composition may include a second AI model 510 or a third AI model 520 together with a first AI model 500. For example, the apparatus 100 for analyzing the body composition may be realized to include the first AI model 500 and the second AI model 510 (FIG. 11), the first AI model 500 and the third AI model 520 (FIG. 12), or all of the first through third AI models 500 through 520(FIG. 13). According to the present embodiment, a case in which the apparatus 100 for analyzing the body composition includes all of the first through third AI models 500 through 520 is described for convenience of explanation.

While the first AI model 500 may be a model configured to segment a body tissue, the second and third AI models 510 and 520 may be models configured to recognize a specific location of a human body. That is, the first AI model 500 may be a segmentation model of a body tissue, and the second and third AI models 510 and 520 may be anatomic localization models.

Figures 6, 7:
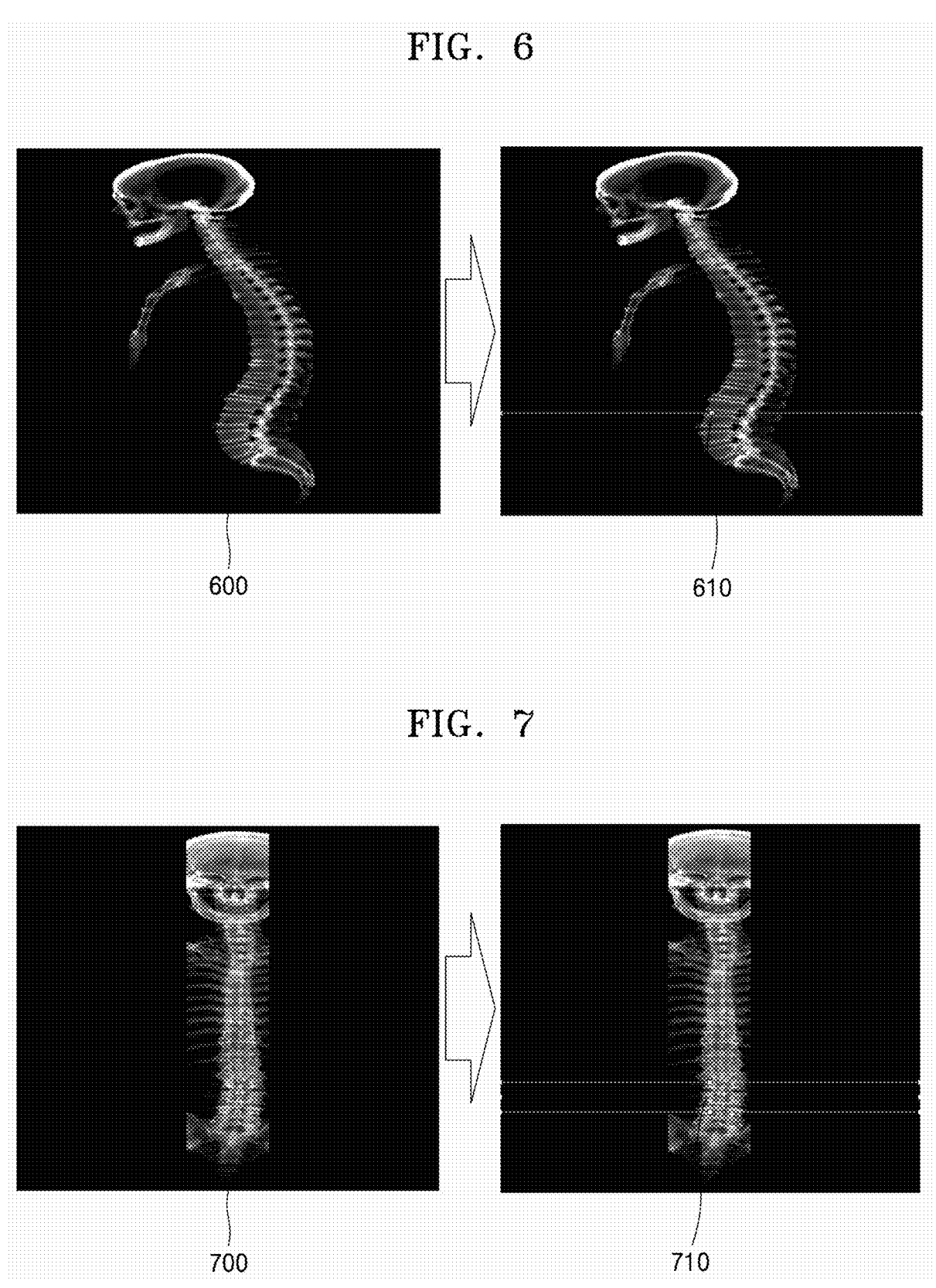
FIG. 6 is a diagram of an example of training data for a second AI model, according to an embodiment.
FIG. 7 is a diagram of an example of learning model for a third AI model, according to an embodiment.

The second AI model 510 may be a model trained by using training data generated by labelling a specific location based on a spine. For example, as illustrated in FIG. 6, the second AI model 510 may be trained by using training data labelling a specific location 610 (for example, the L3 location) of the spine based on a sagittal plane of the spine. In this case, when the second AI model 510 on which training is completed receives information about a spine (for example, a spine image, voxel data about a spinal region, etc.), the second AI model 510 may predict and output the L3 location 550.

The third AI model 520 may be a model trained by using training data generated by labelling a predetermined region based on the spine. For example, the third AI model 520 may be trained by using the training data labelling a sectional region 710 of the spine (for example, a waist sectional region) based on a coronal plane of the spine, as illustrated in FIG. 7. In this case, when the third AI model 520 on which training is completed receives information about a bone (for example, a bone image, voxel data about a bone region, etc.), the third AI model 520 may predict and output the waist sectional region 560 between the rib and the pelvis.

The apparatus 100 for analyzing the body composition may generate information about a bone region 540 (for example, a spinal region) to be input into the second AI model 510 or the third AI model 520, by using the first AI model 500. For example, the apparatus 100 for analyzing the body composition may segment the bone region 540 including the spine from the examination medical image 530, by using the first AI model 500 trained to be able to segment a bone region along with a body tissue, such as a skin, an internal organ, fat, muscle, etc.

For example, the apparatus 100 for analyzing the body composition may generate the information about the bone region 540, in which a voxel value of the bone region 540 segmented from the examination medical image 530 is configured as "1," and a voxel value of other regions of the examination medical image 530 is configured as "0," and then, may input the information about the bone region 540 into the second AI model 510 or the third AI model 520 to identify a specific location or a specific region of the examination medical image 530. Here, the voxel values "1" and "0" are values for distinguishing the bone region 540 and the other regions from each other, and are not limited thereto. Voxel values may be configured in various forms to distinguish the bone region and the other regions from each other in the examination medical image 530. According to another embodiment, the apparatus 100 for analyzing the body composition may generate the information about the bone region 540, in which the voxel value of the bone region in the examination medical image 530 is intactly maintained, and the voxel value of the other regions in the examination medical image 530 is configured as "0."

The apparatus 100 for analyzing the body composition may recognize and output the body composition of a predetermined location or a predetermined region of a human body, based on the predetermined location or the predetermined region of the examination medical image that is identified through the second AI model 510 or the third AI model 520. For example, when the examination medical image 530 includes a plurality of CT images with respect to the whole human body or an abdominal region, the apparatus 100 for analyzing the body composition may recognize a CT image corresponding to a predetermined location, from among the plurality of CT images included in the examination medical image 530, or a plurality of CT images corresponding to a predetermined region, by using the second AI model 510 or the third AI model 520. The apparatus 100 for analyzing the body composition may recognize the body composition based on a body tissue segmented from the plurality of CT images corresponding to the predetermined location or the predetermined region. For example, a predetermined location 550 may be a navel location (for example, the L3 location of the spine) defined based on the spine, and a predetermined region 560 may be an abdominal region (for example, a region between the rib and the pelvis) defined based on the spine.

FIG. 6 is a diagram of an example of training data for the second AI model according to an embodiment.

Referring to FIG. 6, the second AI model is a model configured to recognize an anatomical location, and thus, the training data for the second AI model may be generated by labelling a predetermined location (for example, the location L3) 610 based on a spine. For example, the apparatus 100 for analyzing the body composition may generate the training data by displaying an image 600 including the spine on a screen and receiving the predetermined location 610 from a user.

Although the present embodiment illustrates the training data displaying the sagittal plane of the spine, the training data does not necessarily have to be a spinal image of the sagittal plane and may include the training data labelling a predetermined location based on a bone region. For example, as illustrated in FIG. 7, the training data labelling a predetermined location based on a coronal plane may be used. Also, to help understanding, the present embodiment illustrates an example of the training data including an image of the entire spine. However, the training data may be generated by labelling a predetermined location based on an image of a part of the bone region, rather than an image of the entire bone region. According to another embodiment, the training data of the second AI model may be generated by using a result of segmenting a body tissue of the first AI model. This aspect will be described again with reference to FIG. 8.

FIG. 7 is a diagram of an example of training data for the third AI model according to an embodiment.

Referring to FIG. 7, the third AI model is a model configured to recognize an anatomical location, and thus, the training data for the third AI model may be generated by labelling a predetermined region (for example, a region between the rib and the pelvis, etc.) based on a bone region. For example, the apparatus 100 for analyzing the body composition may generate the training data by displaying a spinal image 700 on a screen and receiving an input of a predetermined region 710 from a user.

The present embodiment illustrates the training data displaying a coronal plane of the bone region. However, the training data is not limited thereto. For example, the training data may be generated by labelling a predetermined region based on an image of the bone region of the sagittal plane as illustrated in FIG. 6. Also, the training data may be generated by labelling a predetermined region with respect to an image of a part of the bone region, rather than an image of the entire bone region. According to another embodiment, the training data of the third AI model may be generated by using a result of segmenting a body tissue of the first AI model. This aspect will be described again with reference to FIG. 8.

Figure 8:
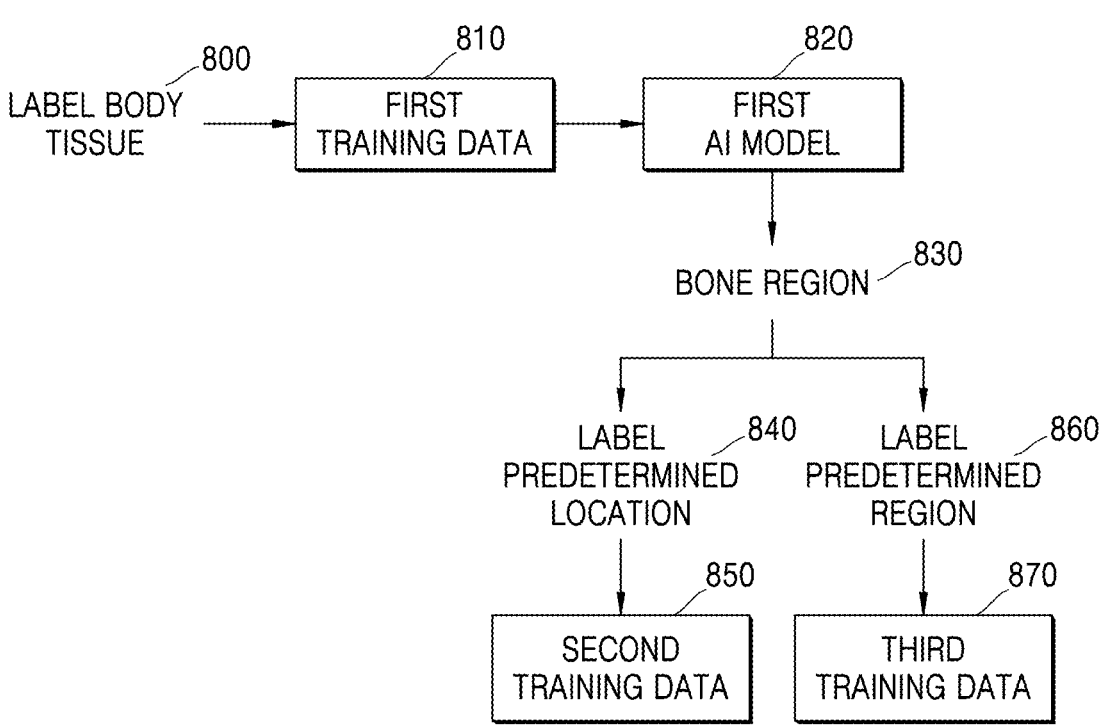
FIG. 8 is a diagram of an example of a method of generating training data for an AI model, according to an embodiment.

FIG. 8 is a diagram of an example of a method of generating training data for an AI model, according to an embodiment.

Referring to FIG. 8, first training data 810 for training a first AI model 820 may be generated by labelling (800) body tissue regions, such as a skin, an internal organ, fat, muscle, bones, etc., in a training medical image. For example, a user may directly segment and label the body tissue regions, such as the skin, the internal organ, the fat, the muscle, etc., in the training medical image. Alternatively, each body tissue may be segmented in the medical image by using various conventional segmentation algorithms that are configured to identify a body tissue, such as a bone, an internal organ, fat, muscle, etc., and the first training data may be automatically generated by labelling information about the fat, the muscle, etc. with respect to the segmented body tissue.

Second training data 850 for training a second AI model and third training data 870 for training a third AI model may be generated by using the first AI model 820. For example, the first AI model 820 may be a model configured to segment a bone region 830 including a spine in a medical image. In this case, the apparatus 100 for analyzing the body composition may generate the second training data 850 or the third training data 870 by displaying, on a screen, a bone (that is, a spine) region segment from a training medical image by using the first AI model 820 and by receiving an input of a predetermined location (for example, the location L3) 840 or a predetermined region (for example, a waist region between the rib and the pelvis) 860 from a user.

FIG. 9 is a diagram of an example of biometric information according to an embodiment.

Referring to FIG. 9, the apparatus 100 for analyzing the body composition may recognize body composition information, such as a skin region, an internal organ region, a skeletal muscular region, a visceral fat region, etc., based on each body tissue segmented through the first AI model and may display the body composition information in various forms, such as a number, a graph, etc.

The apparatus 100 for analyzing the body composition may segment the body tissue, such as fat, muscle, etc., in a medical image in which a cross-section of a human body is captured, and thus, may segment the body composition information based on the cross-section of the human body and display the body composition information for each location of the cross-section (900). According to another embodiment, the apparatus 100 for analyzing the body composition may output the body composition information in the form of an image file or an Excel file of the Microsoft Company.

Figure 10:
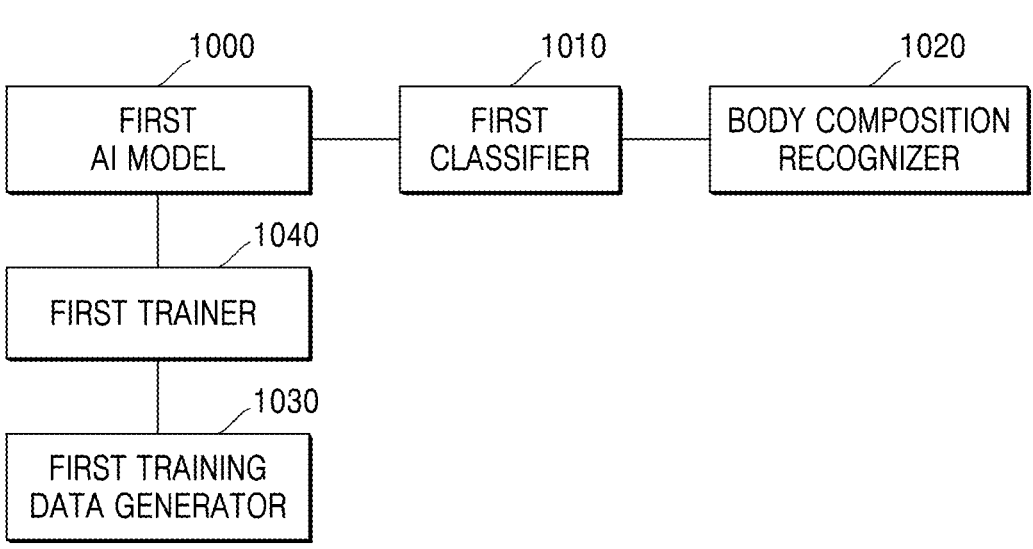
FIG. 10 is a diagram of components according to a first embodiment of an apparatus for analyzing a body composition according to an embodiment.

FIG. 10 is a diagram of components according to a first embodiment of the apparatus 100 for analyzing the body composition according to an embodiment.

Referring to FIG. 10, the apparatus 100 for analyzing the body composition may include a first AI model 1000, a first classifier 1010, a body composition recognizer 1020, a first training data generator 1030, and a first trainer 1040. When the apparatus 100 for analyzing the body composition uses the first AI model 1000 previously trained, the first training data generator 1030 and the first trainer 1040 may be omitted.

The first AI model 1000 is a model configured to segment a body tissue, such as a skin, an internal organ, a bone, fat, muscle, or the like, when receiving an examination medical image. An example of the first AI model 1000 is illustrated in FIGS. 3 and 4.

The first classifier 1010 may segment at least one body tissue, such a skin, an internal organ, a bone, fat, muscle, or the like, by inputting an examination medical image to the trained first AI model 1000. For example, when the examination medical image includes a plurality of CT images in which a cross-section of a human body is captured, the first classifier 1010 may obtain a result of segmenting each body tissue, such as fat, muscle, or the like, from each CT image included in the examination medical image, by inputting each CT image to the first AI model 1000.

The body composition recognizer 1020 may recognize and output body composition information, such as a region, a volume, a weight, a texture, etc. of a skin, an internal organ, a bone, fat, muscle, or the like, based on the body tissue segmented by the first classifier 1010 in the examination medical image.

The first training data generator 1030 may generate first training data labelling a body tissue region, such as a skin, an internal organ, a bone, fat, muscle, or the like, in a training medical image. For example, the first training data generator 1030 may generate the training data by displaying the training medical image on a screen and receiving an input of each body tissue region from a user. Alternatively, the first training data generator 1030 may generate the first training data by automatically segmenting and labelling each region in the training medical image by applying various conventional region segmentation algorithms that are configured to segment each body tissue region.

The first trainer 1040 may train the first AI model 1000 by using the first training data.

Figure 11:
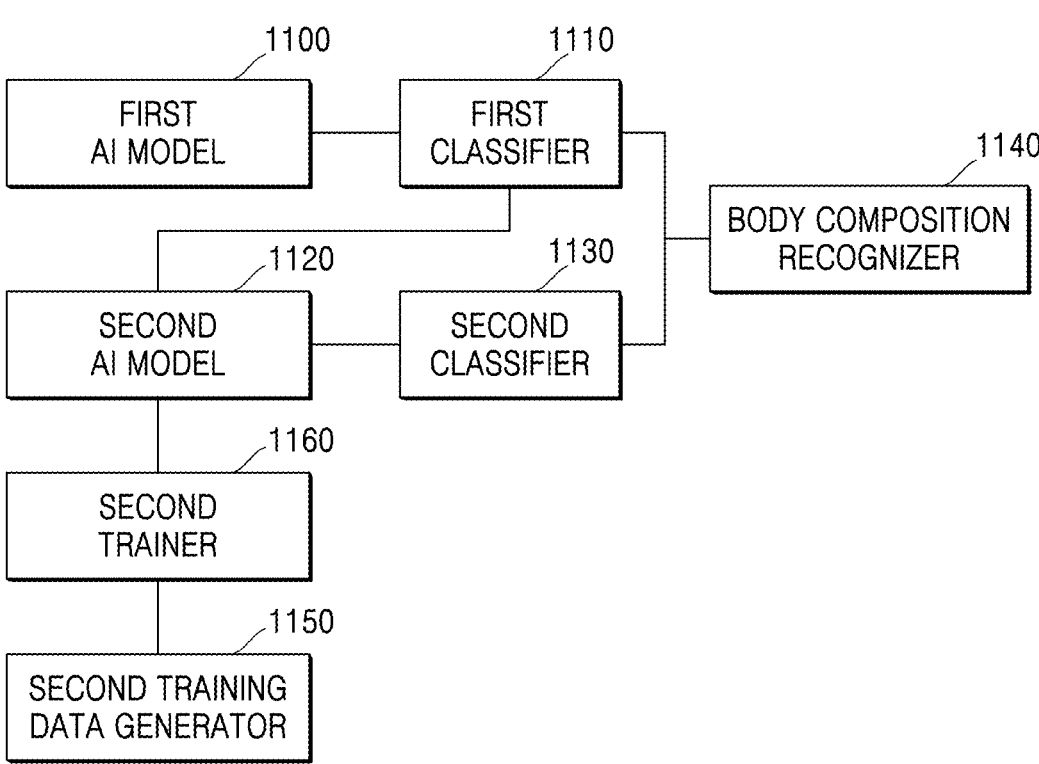
FIG. 11 is a diagram of components according to a second embodiment of an apparatus for analyzing a body composition according to an embodiment.

FIG. 11 is a diagram of components according to a second embodiment of the apparatus 100 for analyzing the body composition according to an embodiment.

Referring to FIG. 11, the apparatus 100 for analyzing the body composition may include a first AI model 1100, a first classifier 1110, a second AI model 1120, a second classifier 1130, a body composition recognizer 1140, a second training data generator 1150, and a second trainer 1160. When the apparatus 100 for analyzing the body composition uses the second AI model 1120 previously trained, the second training data generator 1150 and the second trainer 1160 may be omitted. According to another embodiment, the apparatus 100 for analyzing the body composition may further include the first training data generator 130 and the first trainer 1040 described with reference to FIG. 10.

The first AI model 1100 and the first classifier 1110 are the same as described above with reference to FIG. 10, and thus, their descriptions are omitted.

The second AI model 1120 is a model configured to recognize and output a predetermined location of a bone region when receiving bone region information. An example of the second AI model 1120 is illustrated in FIGS. 5 and 6.

The second classifier 1130 may recognize a predetermined location by inputting the bone region information to the second AI model 1120. For example, the second classifier 1130 may recognize the L3 location by inputting spinal information to the second AI model configured to output the L3 location of the spine. The spinal information input into the second AI model 1120 may be information (for example, a bone image including the spine or voxel information of the bone region) about the bone region in the examination medical image, which is segmented by the first classifier 1110 by using the first AI model 1100. For example, the first AI model 1100 may be a model configured to segment not only the body tissue, such as fat, muscle, etc., but also the bone region, in the examination medical image, and the second classifier 1130 may input the information with respect to the bone region output by the first classifier 1110, into the second AI model 1120, to recognize a predetermined location in the examination medical image.

The body composition recognizer 1140 may recognize and output body composition information corresponding to a predetermined location of a human body, based on the examination medical image corresponding to the predetermined location recognized by the second classifier 1120 and the body tissue region information of the examination medical image that is segmented by the first identifier 1110.

The second training data generator 1150 may generate second training data for the second AI model 1120. The second training data may be generated by labelling a predetermined location in an image of the entire spine or an image of a part of the spine. For example, the second training data generator 1150 may generate the second training data by using the bone region segmented from the training medical image through the first AI model 1100. An example of the method, performed by the second AI model 1120, of generating the second training data by using the first AI model 1100 is illustrated in FIG. 8.

The second trainer 1160 may train the second AI model 1120 by using the second training data.

Figure 12:
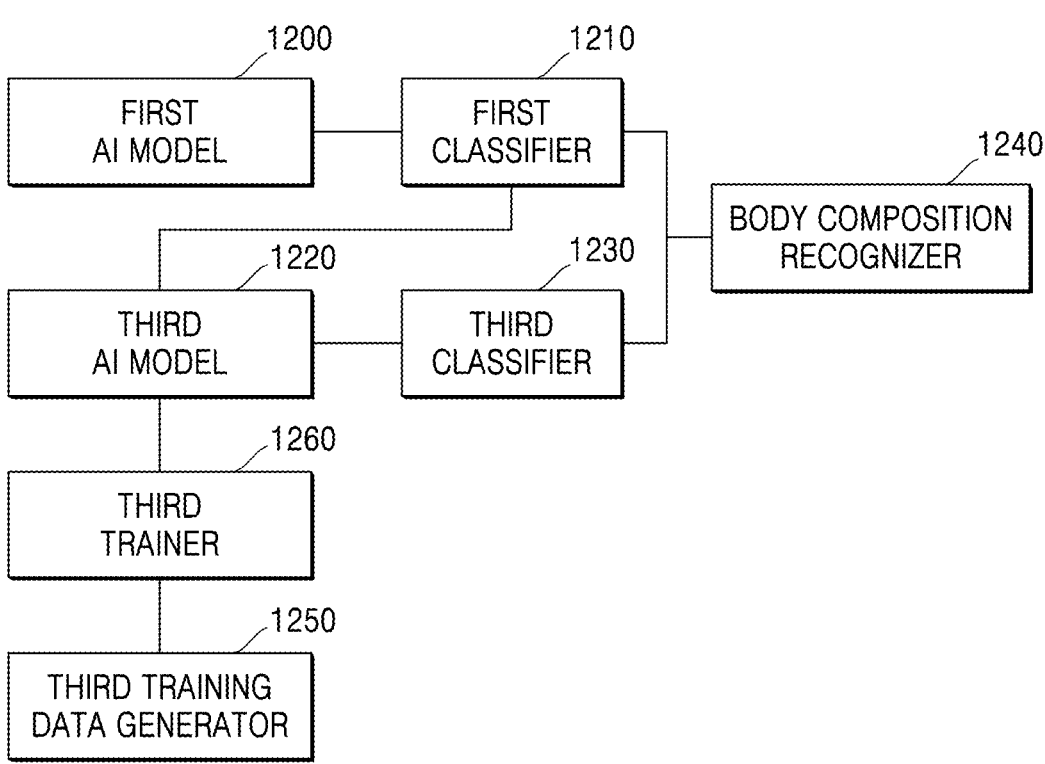
FIG. 12 is a diagram of components according to a third embodiment of an apparatus for analyzing a body composition according to an embodiment.
Figure 13:
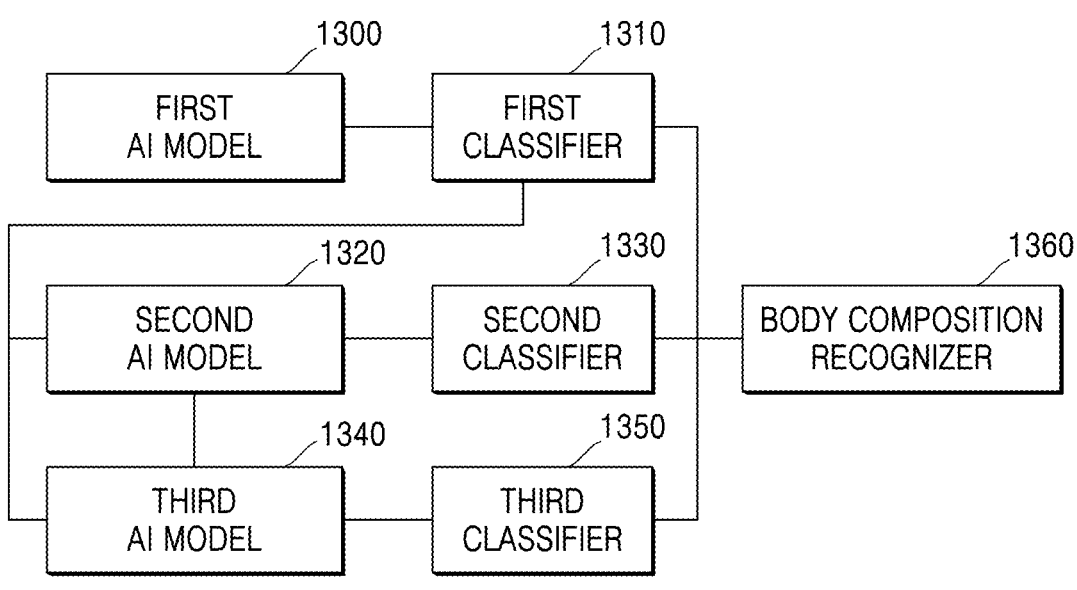
FIG. 13 is a diagram of components according to a fourth embodiment of an apparatus for analyzing a body composition according to an embodiment.

FIG. 12 is a diagram of components according to a third embodiment of the apparatus 100 for analyzing the body composition according to an embodiment.

Referring to FIG. 12, the apparatus 100 for analyzing the body composition may include a first AI model 1200, a first classifier 1210, a third AI model 1220, a third classifier 1230, a body composition recognizer 1240, a third training data generator 1250, and a third trainer 1260. When the apparatus 100 for analyzing the body composition uses the third AI model 1220 previously trained, the third training data generator 1250 and the third trainer 1260 may be omitted. According to another embodiment, the apparatus 100 for analyzing the body composition may further include the first training data generator 130 and the first trainer 1040 described with reference to FIG. 10.

The first AI model 1200 and the first classifier 1210 are the same as described with reference to FIG. 10, and thus, their descriptions are omitted.

The third AI model 1220 is a model configured to recognize and output a predetermined region of a spine, when receiving spinal information. An example of the third AI model 1220 is illustrated in FIGS. 5 and 7.

The third identifier 1230 may recognize a predetermined region by inputting the spinal information to the third AI model 1220. For example, the third classifier 1230 may recognize an abdominal region in the examination medical image by inputting the spinal information to the third AI model configured to output predetermined top and bottom regions (that is, the abdominal region) based on the L3 location of the spine. The spinal information input into the third AI model 1220 may be information about a spinal region segmented by the first identifier 1210. For example, the first AI model 1200 may be a model configured to segment not only the body tissue, such as fat, muscle, etc., but also the bone region, in the examination medical image, and the third classifier 1230 may input information of the bone region output by the first identifier 1210 into the third AI model 1220 to recognize a predetermined region of the examination medical image.

The body composition recognizer 1240 may recognize body composition information corresponding to a predetermined region of a human body, based on the examination medical image to corresponding to the predetermined region recognized by the third classifier 1230 and the body tissue region information of the examination medical image that is segmented by the first classifier 1210.

The third training data generator 1250 may generate third training data for the third AI model 1220. The third training data may be generated by labelling a predetermined region in an image of the entire spine or an image of a part of the spine. For example, the third training data generator 1250 may generate the third training data by using the bone region segmented from the training medical image through the first AI model 1200. An example of a method of generating the third training data by using the first AI model 1200 is illustrated in FIG. 8.

The third trainer 1260 may train the third AI model 1220 by using the third training data.

FIG. 13 is a diagram of components according to a fourth embodiment of the apparatus 100 for analyzing the body composition according to an embodiment.

Referring to FIG. 13, the apparatus 100 for analyzing the body composition may include a first AI model 1300, a first classifier 1310, a second AI model 1320, a second classifier 1330, a third AI model 1340, a third classifier 1350, and a body composition recognizer 1360. According to another embodiment, the apparatus 100 for analyzing the body composition may further include trainers configured to train the AI models 1300, 1320, and 1340, respectively.

The first AI model 1300 and the first classifier 1310 are the same as described with reference to FIG. 10, and the second AI model 1320 and the second classifier 1330 are the same as described with reference to FIG. 11. Also, the third AI model 1340 and the third classifier 1350 are the same as described with reference to FIG. 12.

The body composition recognizer 1360 may recognize body composition information with respect to a predetermined location or a predetermined region of a human body based on body tissue region information with respect to an examination medical image, which is segmented through the first classifier 1310, predetermined location information with respect to the examination medical image, which is recognized through the second classifier 1330, and predetermined region information with respect to the examination medical image, which is recognized through the third classifier 1350.

Figure 14:
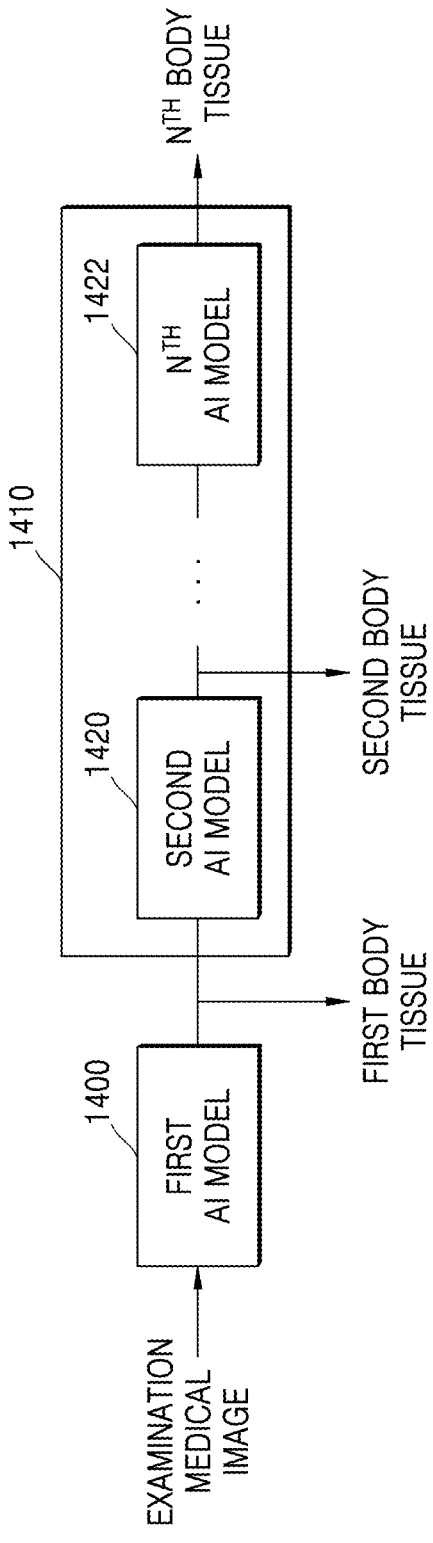
FIG. 14 is a diagram of an example of a method of segmenting a body tissue, according to an embodiment.

FIG. 14 is a diagram of an example of a method of segmenting a body tissue, according to an embodiment.

Referring to FIG. 14, the apparatus 100 for analyzing the body composition may include a first AI model 1400 and a cascade model 1410. The first AI model 1400 may be the same as the first AI model 300 described with reference to FIG. 3. The cascade model 1410 may have a structure in which one or more AI models 1420 and 1422 are sequentially connected. An output value of the second AI model 1420 may become an input value of the third AI model, and based on this manner, an output value of an $N-1^{th}$ AI model may become an input value of an $N^{th}$ AI model 1422. The number of AI models 1420 and 1422 sequentially connected in the cascade model 1410 may be variously modified, according to an embodiment. However, the cascade model 1410 may include one AI model 1420 as well.

The second AI model 510 and the third AI model 520 described with reference to FIG. 5, etc. are models configured to recognize an anatomical location of a human body. However, the plurality of AI models 1420 and 1422 sequentially connected in the cascade model 1410 according to the present embodiment are models configured to sub-divide a body tissue segmented by the first AI model. In other words, the first AI model 1400 may be a model configured to segment at least one body tissue region from among a skin, a bone, an internal organ, a blood vessel, muscle, and fat in a medical image, and the cascade model 1410 may be a model configured to sub-divide the body tissue segmented by the first AI model 1400.

According to an embodiment, the first AI model 1400 may be a model configured to segment muscle from the medical image, and the cascade model 1410 may be a model configured to sub-divide the muscle segmented by the first AI model 1400 into muscles of lower limb and muscles of upper limb. The sub-division may be different according to the number of AI models 1420 and 1422 included in the cascade model 1410. For example, when the cascade model includes two AI models, the second AI model 1420 may be a model configured to sub-divide muscles into a body, a leg, an arm, etc., and the third AI model may be a model configured to sub-divide the leg muscles again into a calf and a thigh.

According to another embodiment, the first AI model 1400 may be a model configured to segment various internal organs from a medical image, and the cascade model 1410 may be a model configured to sub-divide the segmented internal organs. For example, when the first AI model 1400 segments a lung tissue from the medical image, the second AI model 1422 of the cascade model 1410 may sub-divide the lung tissue into a right lung and a left lung, and the third AI model may sub-divide the right lung into a superior lobe, an inferior lobe, and a middle lobe.

According to another embodiment, the first AI model 1400 may be a model configured to segment a bone region from the medical image, and the second AI model 1422 of the cascade model 1410 may be a model configured to segment a spinal bone region from the bone region, and the third AI model may be a model configured to sub-divide the spinal bone into a cervical spine, a thoracic spine, and a lumbar spine.

The first AI models 1000, 1100, 1200, and 1300 of FIGS. 10 through 13 may be replaced by the first AI model 1400 and the cascade model 1410 according to the present embodiment. In this case, the first classifiers 1010, 1110, 1210, and 1310 of FIGS. 10 through 13 may segment a first body tissue from an examination medical image, by using the first AI model 1400, and may obtain second through $N^{th}$ body tissues which are sub-divided from the first body tissue, by using each of the AI models 1420 and 1422 of the cascade model 1410. The body composition recognizers 1020, 1140, 1240, and 1360 may recognize a body composition by using at least one of the first through $N^{th}$ body tissues. For example, in the case of models configured to recognize muscles, the body composition recognizers 1020, 1140, 1240, and 1360 may recognize the amount of muscles of the entire human body by using a first body tissue region obtained by the first AI model, may recognize the amount of muscles of arms or legs by using a second body tissue region obtained by the second AI model, and may recognize the amount of muscles of a calf and a thigh by using a third body tissue region obtained by the third AI model.

According to another embodiment, the first AI model may be connected to a plurality of cascade models, and a second AI model of each of the cascade models may be connected to a plurality of third AI models to form a tree structure. For example, when the first AI model is a model configured to segment each of a bone, fat, and muscle, there may be first through third cascade models respectively sub-dividing the bone, the fat, and the muscle. When the first cascade model is a model configured to segment the bone, and the second AI model of the first cascade model is a model configured to sub-divide the bone into the spine and the rib, the second AI model of the first cascade model may be connected to a $3\text{-}1^{st}$ AI model configured to sub-divide the spine and a $3\text{-}2^{nd}$ AI model configured to sub-divide the rib. As described above, according to the number of sub-divided body tissues and the number of sub-divisions, AI models having various tree-shaped connection relationships may be generated.

The disclosure may also be realized as a computer-readable code in a computer-readable recording medium. The computer-readable recording medium includes all types of recording devices in which data which may be read by a computer system is stored. Examples of the computer-readable recording medium include read-only memories (ROMs), random-access memories (RAMs), CD-ROMs, magnetic tapes, floppy disks, optical data storage devices, etc. The computer-readable recording medium can also be distributed over network coupled computer systems so that the compute readable code is stored and executed in a distributed fashion.

One or more embodiments of the disclosure are described above. It would be understood by one of ordinary skill in the art that the disclosure may be realized in a different form modified within a range not departing from the essential properties of the disclosure. Therefore, the embodiments should be considered in a descriptive sense only and not for purposes of limitation. The scope of the disclosure is defined not by the detailed description of the disclosure but by the appended claims, and all differences within the scope will be construed as being included in the disclosure.

The invention claimed is:

1. A method of analyzing a body composition by using a medical image, the method comprising:
   training a first artificial intelligence model by using training data labelling at least one body tissue region from among a skin, a bone, an internal organ, a blood vessel, muscle, and fat in a training medical image;
   receiving an examination medical image;
   segmenting a body tissue from the examination medical image by using the first artificial intelligence model;
   recognizing a predetermined location or region of a spine by inputting, to a second artificial intelligence model or a third artificial intelligence model, a bone region of the examination medical image that is segmented through the first artificial intelligence model,
   wherein the second artificial intelligence model is trained by using training data labelling the predetermined location of a spine,
   wherein the third artificial intelligence model is trained by using training data labelling the predetermined region of a spine; and
   outputting body composition information recognized based on a region, a volume, or a weight of visceral fat corresponding to the predetermined location or region of the examination medical image,
   further comprising:
   displaying a spine region segment from the training medical image by using the first artificial intelligence model;
   receiving an input of the predetermined location or region of the spine region segment from a user; and
   generating the training data of the second artificial intelligence model or the third artificial intelligent model by labelling the predetermined location or region in the spine region segment.

2. The method of claim 1, wherein
   the segmenting the body tissue comprises inputting a first body tissue segmented by the first artificial intelligence model to a cascade model in which one or more artificial intelligence models are sequentially connected, and sub-dividing the first body tissue into a second body tissue, and
   the outputting of the body composition information comprises recognizing the body composition information about at least one of the first body tissue and the second body tissue.

3. The method of claim 2, wherein the cascade model comprises at least two artificial intelligence models sequentially connected.

4. The method of claim 1, wherein the training medical image or the examination medical image is a computed tomography (CT) image in which an entirety or a predetermined region of a human body is captured.

5. The method of claim 1, wherein the outputting of the body composition information comprises outputting the body composition information by marking the body composition information with respect to a cross-section of a human body for each location of the cross-section.

6. The method of claim 1, wherein the training of the first artificial intelligence model comprises training the first artificial intelligence model by using training data labelling at least one region from among a skin, a bone, an internal organ, a blood vessel, muscle, and fat.

7. The method of claim 1, wherein the predetermined region is an abdominal region defined based on the spine.

8. A non-transitory computer-readable recording medium having recorded thereon a computer program for executing the method of claim 1.

9. An apparatus for analyzing a body composition, the apparatus comprising:

a first artificial intelligence model trained by using training data labelling at least one body tissue region from among a skin, a bone, an internal organ, a blood vessel, muscle, and fat in a medical image;

a first classifier configured to segment a body tissue, such as the muscle, the fat, or the bone, by inputting an examination medical image to the first artificial intelligence model;

a body composition recognizer configured to recognize and output body composition information based on the segmented body tissue;

a second artificial intelligence model trained by using training data labelling a predetermined location of a spine;

a second classifier configured to recognize a predetermined location of the spine by inputting, to the second artificial intelligence model, a bone region of the examination medical image that is segmented through the first artificial intelligence model; and a second training data generator configured to:

display a spine region segment from a training medical image by using the first artificial intelligence model;

receive an input of the predetermined location of the spine region segment from a user; and generate the training data of the second artificial intelligence model by labelling the predetermined location in the spine region segment, wherein the body composition recognizer is further configured to recognize the body composition information comprising visceral fat of a cross-section with respect to the predetermined location of the spine recognized by the second classifier.

10. The apparatus of claim 9, further comprising a cascade model in which one or more artificial intelligence models are sequentially connected, wherein the first classifier is further configured to subdivide a first body tissue segmented by the first artificial intelligence model into at least one second body tissue by inputting the first body tissue to the cascade model, and the body composition recognizer is further configured to recognize the body composition information with respect to at least one of the first body tissue and the second body tissue.

11. The apparatus of claim 9, further comprising:

a first training data generator configured to generate the training data of the first artificial intelligence model by labelling the at least one body tissue region from among the skin, the bone, the internal organ, the blood vessel, the muscle.

12. The apparatus of claim 9, further comprising:

a third artificial intelligence model trained by using training data labelling a predetermined region based on a spine; and a third classifier configured to identify a predetermined region by inputting a bone region of the examination medical image to the third artificial intelligence model, wherein the body composition recognizer is further configured to recognize the body composition information with respect to the predetermined region identified by the third classifier.

13. The apparatus of claim 12, further comprising:

a first training data generator configured to generate the training data of the first artificial intelligence model by labelling the at least one body tissue region from among the skin, the bone, the internal organ, the blood vessel, the muscle, and the fat in the medical image; and a third training data generator configured to generate the training data of the third artificial intelligence model by labelling the predetermined region in the bone region segmented by the first artificial intelligence model.

* * * * *